United States Patent
Fort et al.

(10) Patent No.: US 6,780,248 B2
(45) Date of Patent: Aug. 24, 2004

(54) APPLICATOR AND METHOD FOR APPLYING ADHESIVE TO ROD-SHAPED MEMBERS SUCH AS COTTON SWABS

(75) Inventors: Wesley C. Fort, Cumming, GA (US); James Keough, Cumming, GA (US); Leslie J. Varga, Cumming, GA (US)

(73) Assignee: Nordson Corporation, Westlake, OH (US)

(*) Notice: Subject to any disclaimer, the term of this patent is extended or adjusted under 35 U.S.C. 154(b) by 0 days.

(21) Appl. No.: 10/273,983

(22) Filed: Oct. 18, 2002

(65) Prior Publication Data

US 2004/0074439 A1 Apr. 22, 2004

(51) Int. Cl.[7] .............................................. B05C 11/00
(52) U.S. Cl. ...................... 118/416; 118/401; 118/428; 118/218; 118/232; 118/107; 118/109; 118/506; 427/355
(58) Field of Search ................................. 118/506, 401, 118/416, 428, 233, 31, 56, 107, 253, 109, 200, 209, 214, 218, 219, 232, 235; 427/207.1, 355; 19/145.3

(56) References Cited

U.S. PATENT DOCUMENTS

| | | | | |
|---|---|---|---|---|
| 3,698,040 A | * | 10/1972 | Mourkakos | ................ 19/145.3 |
| 3,999,509 A | * | 12/1976 | Lucas | ........................... 118/47 |
| 4,425,866 A | * | 1/1984 | Hoffmann | ..................... 118/58 |
| 4,705,551 A | * | 11/1987 | Robinson, Jr. | ............... 65/60.1 |
| 5,788,772 A | * | 8/1998 | Kunieda et al. | ............ 118/264 |
| 6,077,351 A | * | 6/2000 | Herzog | ........................ 118/414 |

OTHER PUBLICATIONS

Nordson Corporation, *Coton Swab Manufacturing*, Application Bulletin, 2 pgs., 10/88.

* cited by examiner

Primary Examiner—Richard Crispino
Assistant Examiner—Michelle Acevedo Lazor
(74) Attorney, Agent, or Firm—Wood, Herron & Evans, L.L.P.

(57) ABSTRACT

A system and method for applying adhesive to at least a first end of a rod-shaped member, such as a cotton swab stick includes a carrier, an adhesive applicator, and a rotator device. The carrier conveys the rod-shaped member or stick in a machine direction and also allows rotation of the rod-shaped member about its longitudinal axis. The adhesive applicator includes an application surface positioned to engage the first end of the rod-shaped member. The application surface includes at least one discharge passage for applying adhesive to the first end of the rod-shaped member. The rotator device rotates the rod relative to the application surface and about its longitudinal axis as the rod-shaped member is conveyed along the application surface.

28 Claims, 4 Drawing Sheets

APPLICATOR AND METHOD FOR APPLYING ADHESIVE TO ROD-SHAPED MEMBERS SUCH AS COTTON SWABS

FIELD OF THE INVENTION

This invention generally relates to the application of adhesive to the ends of rod-shaped members and, more particularly, to the ends of rods or sticks used for manufacturing of cotton swabs.

BACKGROUND OF THE INVENTION

Various manufacturing processes involve affixing elements to one or both ends of a rod-shaped member. One specific application for such a process is the manufacture of cotton swabs. Such products may be manufactured with cotton fibers or other types of fibers secured to one or both ends of a paper, plastic or wooden stick with adhesive. During manufacture, it is important to properly apply the adhesive to one or both ends of the stick before application of the cotton fibers. Too little adhesive will result in unsatisfactory adherence of the fibers to the stick, while excessive adhesive application will result in undesirable manufacturing downtime due to the clean up of adhesive dripping or otherwise being flung from the stick during the manufacturing process. While meeting the precise quantity requirements of adhesive application, the manufacturing process must also consistently apply the adhesive around the end or ends of each stick and must do so in a high speed manufacturing environment to hold product manufacturing costs as low as possible.

One current process for manufacturing cotton swabs involves rapidly conveying the sticks past a rotating wheel which has a lower portion thereof in contact with a container of adhesive. The adhesive therefore continually coats the circumference of the wheel. As the ends of each stick contact the upper portion of the spinning wheel, the ends are simultaneously rotated and coated with the adhesive. While this method allows for a rapid production speed, the above noted problems exist with this type of process. Specifically, the wheel can accumulate too much adhesive on its circumference and, therefore, apply too much adhesive to the ends of the stick. Some of this adhesive will fall or be flung off the ends of the stick necessitating manufacturing downtime in order to clean up the excess adhesive. Also, because the adhesive is exposed to the environment prior to its application on the stick, the adhesive can accumulate various airborne contaminates. This can reduce the effectiveness of the adhesive and lead to unsatisfactory adherence of the fibers to the stick. The use of a wheel to apply adhesive to the sticks may also lead to inconsistent adhesive deposition as a result of inconsistent amounts of adhesive on the circumference of the wheel. For example, as the level of adhesive in the adhesive supply becomes reduced, there may be less adhesive applied to the circumference of the wheel and, conversely, when the supply is increased, increased adhesive contact is made with the wheel resulting in increased amounts of adhesive on the wheel. These characteristics of this existing process correspondingly result in decreased or increased amounts of adhesive being applied to the ends of the sticks.

Another previously proposed manufacturing method for cotton swabs generally involves the use of an on/off adhesive dispensing valve having slot nozzles positioned in the respective paths of the ends of the sticks. The sticks move over the slot nozzles which are activated and the sticks simultaneously rotate such that the ends of the sticks receive the discharged adhesive. The challenge associated with this proposed method is that the rod or stick must be rotated quickly enough as it passes the slot nozzles to ensure coating of the entire circumference of each end. In order for this to occur, line speeds may have to be reduced to an undesirably low level or spinning rates of the sticks may have to be increased to an impractically high level. Even if the speeds are adjusted to ensure a full rotation directly over the slot nozzle, the slot nozzle may still not apply adhesive in an evenly distributed amount to the entire outer surface of each stick end.

For these and other reasons, it would be desirable to provide a system and method for applying adhesive to one or both ends of a rod-shaped member in a uniform, consistent manner, and in precise amounts, while maintaining the high manufacturing speeds necessary to hold down product manufacturing costs.

SUMMARY OF THE INVENTION

In one general aspect, the present invention provides a system for applying adhesive to at least a first end of a rod-shaped member. The system generally includes a carrier, an adhesive applicator, and a rotator device. The carrier is configured to convey the rod-shaped member in a machine direction while allowing rotation of the rod-shaped member about its longitudinal axis. The adhesive applicator preferably includes an application surface positioned to engage the first end of the rod-shaped member. At least one adhesive discharge passage is provided to apply adhesive to the first end. For example, the discharge passage may extend through the application surface to apply adhesive to the first end. The rotator device is positioned preferably on a generally opposite side of the rod-shaped member relative to the application surface and rotates the rod-shaped member about its longitudinal axis as the rod-shaped member is conveyed along the application surface.

The application surface is preferably elongate in the machine direction and angled toward the carrier. The application surface has at least a portion that engages the first end for at least substantially an entire revolution thereof in order to evenly distribute the adhesive around the first end. The rotator device is preferably a stationary belt or other friction inducing surface configured to engage an area of the rod-shaped member other than the first end. For example, in the preferred embodiment, the belt contacts the central area of the rod-shaped member, e.g., the stick of a cotton swab, but does not contact the ends of the rod-shaped member which receive the adhesive and later receive the cotton fibers. Angling the application surface toward the carrier allows the belt to apply pressure to the center of the rod-shaped member while ensuring that the ends thereof maintain contact with the application surface. This helps ensure uniform adhesive application. As the rod-shaped member approaches the application surface, it is moved in a direction toward the rotator device, such as the belt. This is accomplished in the preferred embodiment by using an inclined surface immediately upstream of the adhesive application surface. Of course, other engagement structure may be used instead and may be partly or wholly provided on the carrier or another portion of the system. Preferably, the carrier includes a slot allowing the rod-shaped member to move upward along the inclined surface until it contacts the belt. Other rotator devices may be used as well.

The application surface preferably has multiple adhesive discharge passages spaced transversely relative to the machine direction and associated grooves extending in the machine direction aligned with the discharge passages and extending downstream therefrom. Thus, the adhesive is initially discharged and applied to the end of the rod-shaped member and the rod-shaped member is rotated by the belt along a downstream portion of the application surface. The grooves help ensure that a uniform thickness of adhesive is distributed, preferably in bands about the entire outer surface of the rod end. The grooves are preferably directly aligned with one or more corresponding adhesive discharge passages.

The carrier can be constructed as a link in a chain-like structure which moves along the manufacturing line at high speed, such as on the order of 2500 cotton swabs per minute. The carrier has slots on opposite sides thereof which receive respective end portions of the rod-shaped member and identical adhesive applicators are positioned on opposite sides of the carrier. One or more on/off dispensing valves are used to supply adhesive to the adhesive discharge passages. A sensor is used to detect the presence of each oncoming rod-shaped member and communicates with a control to ensure proper timing of the activation of the valve(s) such that the adhesive is dispensed effectively onto the ends of the rod-shaped member.

The invention further contemplates methods of applying adhesive to at least a first end of a rod shaped member. The method generally involves conveying the rod-shaped member in a machine direction with the longitudinal axis thereof extending transverse to the machine direction. The rod-shaped member is rotated about its longitudinal axis and adhesive is applied to the first end thereof from an adhesive discharge passage in an adhesive application surface. Contact is maintained between the rotating first end of the rod-shaped member and the adhesive application surface downstream of the discharge passage to distribute the discharged adhesive around the first end. The methods of this invention also generally contemplate the processes of using other novel aspects of this invention.

These and other features and objectives of the present invention will become more readily apparent from the following detailed description taken in conjunction with the accompanying drawings.

DETAILED DESCRIPTION OF SPECIFIC EMBODIMENTS

Figure 1:
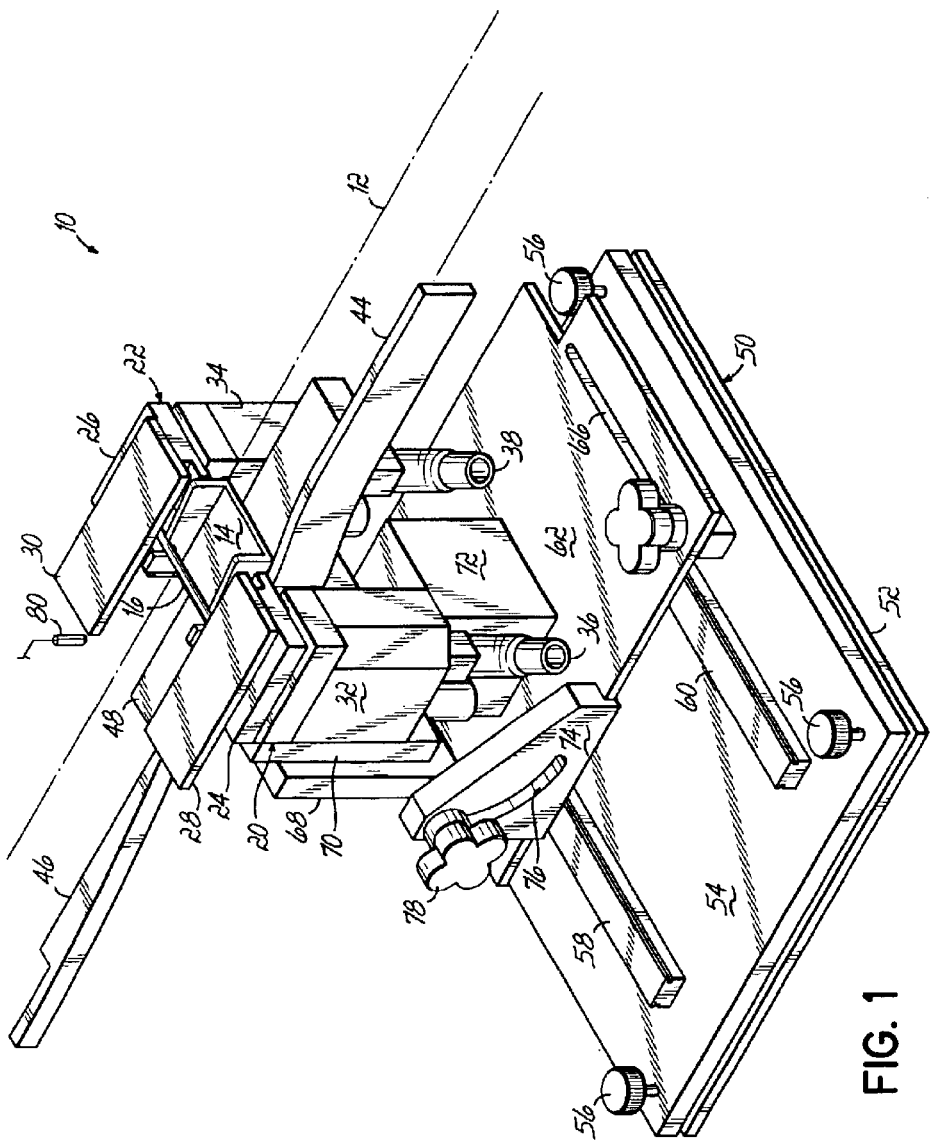
FIG. 1 is a perspective view of a system for applying adhesive to opposite ends of rod-shaped members, such as cotton swab sticks.

FIG. 1 illustrates a system 10 constructed in accordance with a preferred embodiment of the invention. System 10 is incorporated into a manufacturing line schematically indicated at 12 and consisting of multiple carriers 14, only one of which is shown in FIG. 1. Each carrier 14 is constructed as a single link in a chain-like conveying structure. Although only one carrier 14 is shown, it will be understood that many carriers will be provided and linked together along manufacturing line 12, with each carrier 14 conveying preferably only one rod-shaped member or stick 16. A pair of applicators 20, 22 are provided on opposite sides of carrier 14 and include respective applicator plates 24, 26 each having a cover plate 28, 30 to capture any excess adhesive during the application process. Applicator plates 24, 26 are supplied with adhesive via respective valves 32, 34 which, in turn, receive adhesive from a supply (not shown) via respective supply conduits 36, 38. Upstream and downstream side guide rails 44, 46 are provided to guide carriers 14 into the adhesive application area between applicators 20, 22. A bottom plate 48 may be used to mount rails 44, 46.

A base support structure 50 mounts the various components described above adjacent manufacturing line 12. Base support structure 50 comprises first and second plates 52, 54. Second plate 54 may be leveled with respect to first plate 52 by leveling knobs 56. Second plate 54 includes a pair of tracks 58, 60. A third plate 62 is mounted for sliding movement back and forth along tracks 58, 60 and may be locked in place by a knob 64 after adjustment is made lengthwise along a slot 66. Appropriate mounting structure is provided between applicators 20, 22 and plate 62. This includes a plate 68 which is coupled to a plate 70 mounted to respective valves 32, 34 and a block 72. A plate 74 allows the angle of applicators 20, 22 to be moved along a slot 76 and then locked into place via a knob 78. This allows access to applicators 20, 22 and valves 32, 34 for maintenance or other purposes. A sensor 80, such as a photocell, is provided in order to detect the presence of on-coming rod-shaped members 16 and is connected with a conventional control to activate valves 32, 34 and thereby dispense adhesive through applicator plates 24, 26 in a proper timed manner. Sensor 80 may be mounted in any suitable manner, such as to plate 28.

Figure 2:
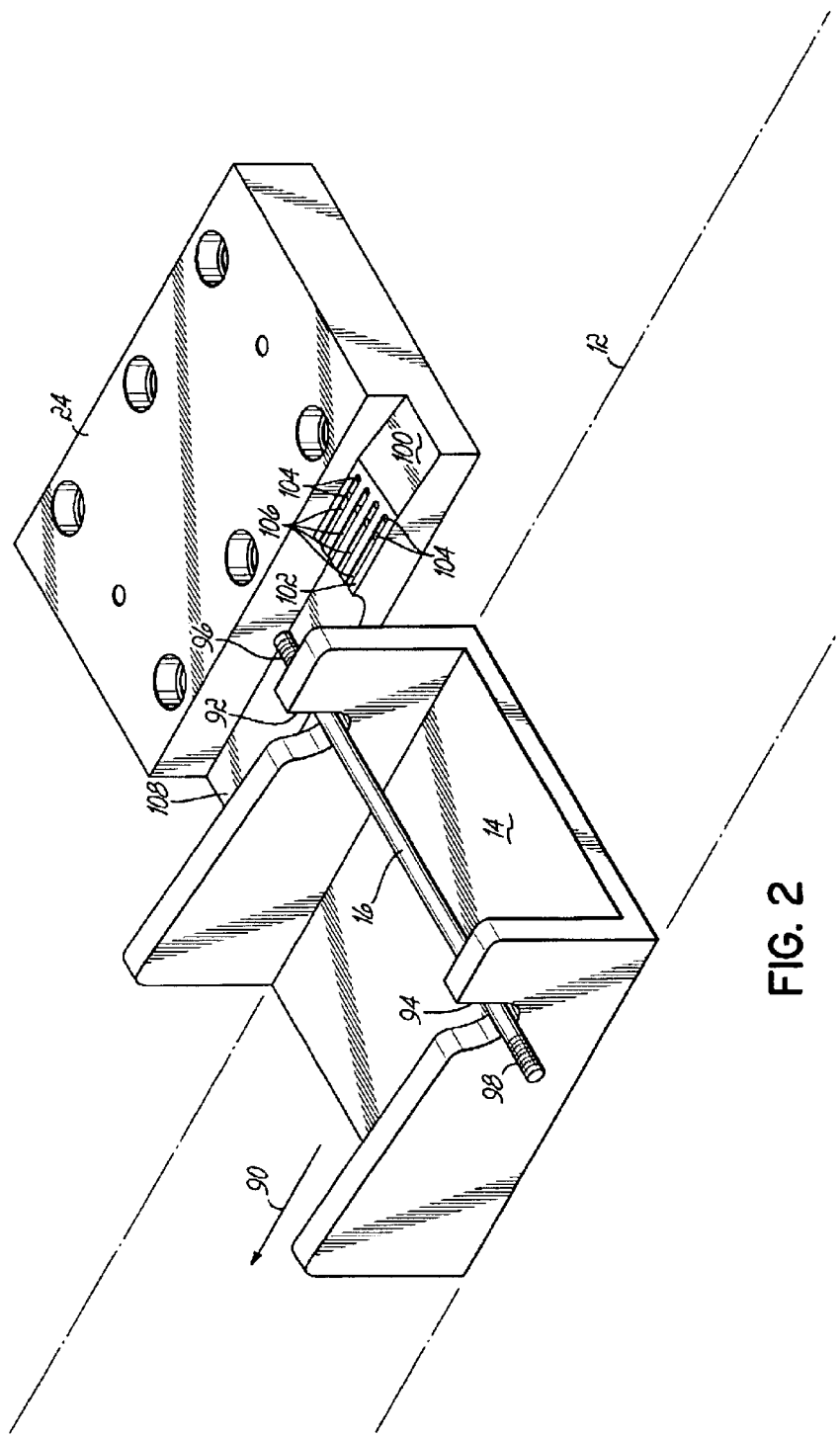
FIG. 2 is a perspective view of a portion of the system shown in FIG. 1, with various components deleted to better illustrate the adhesive application surface and carrier of the system.

FIG. 2 illustrates applicator plate 24 and carrier 14 in greater detail. Although such detail will be described only with respect to applicator plate 24, it will be understood that the structure and operation of applicator plate 22, along with its associated components, is identical. Also, although the preferred system 10 is configured to manufacture cotton swabs having adhesive and fibers placed at both ends of a stick or rod-shaped member, it will be appreciated that other applications will necessitate adhesive and fibers or other elements applied at only one end. Carrier 14 moves in a machine direction indicated by arrow 90 and includes slots 92, 94 on opposite sides for receiving rod-shaped member or stick 16. Rod-shaped member 16 is positioned such that respective ends 96, 98 thereof extend outward from carrier 14 as shown. Applicator plate 24 further includes an upstream inclined surface 100 and application surface 102 located farther in a downstream direction and including a plurality of adhesive discharge passages 104 contained in upstream ends of respective grooves 106. In the preferred embodiment, two discharge passages 104 extend through the upstream end of each groove 106. Farther downstream, a recessed surface 108 is positioned to be out of contact with end 96 of rod-shaped member 16.

Figure 3:
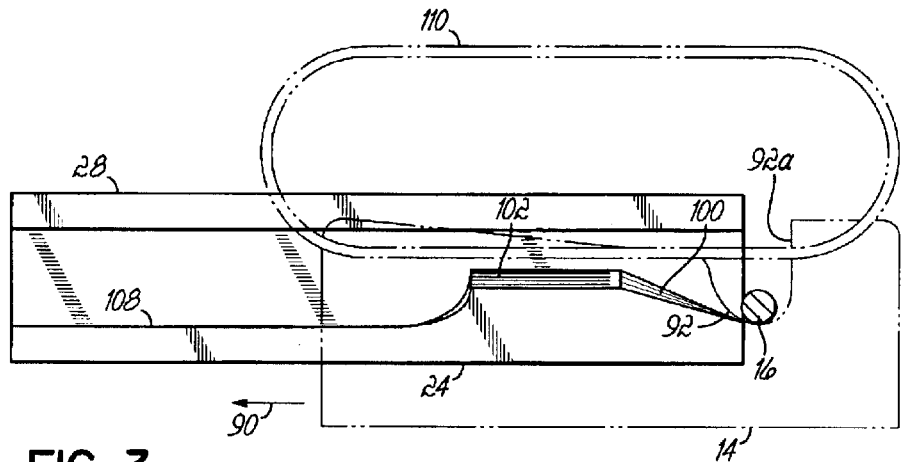
FIGS. 3–6 are schematic side cross sectional views successively illustrating the movement of the cotton swab stick through the process of coating one of its ends with adhesive.
Figure 4:
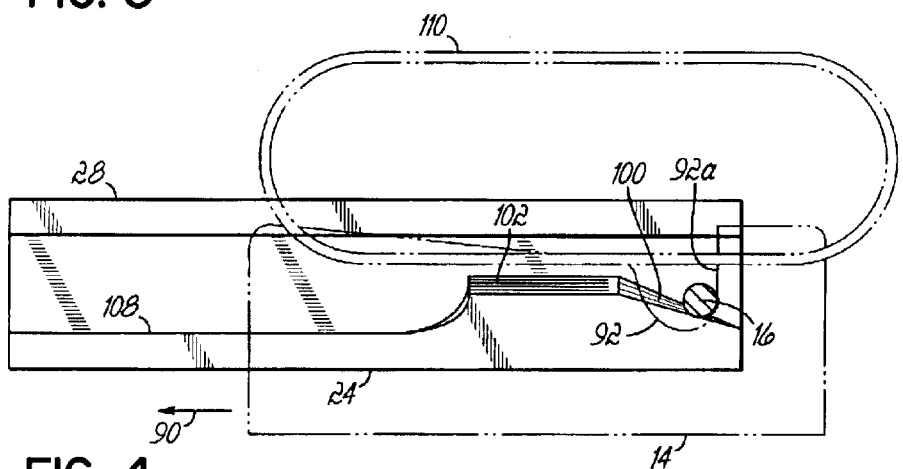
Figure 5:
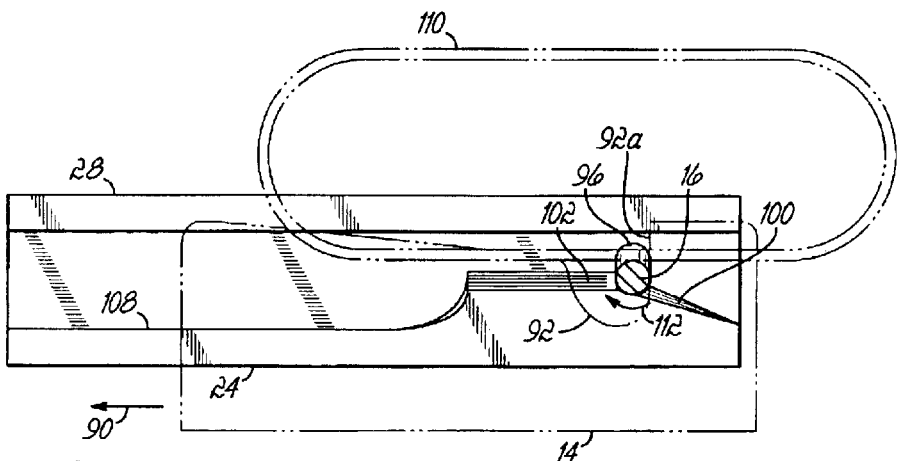

FIGS. 3–6 illustrate the progression of rod-shaped member 16 past inclined surface 100 and adhesive application surface 102. As shown in FIG. 3, carrier 14 moves in machine direction 90 from right to left and rod-shaped member 16 makes initial contact with inclined surface 100. As shown in FIG. 4, rod-shaped member 16 rides up the rear surface 92a of slot 92 as it travels up on inclined surface 100. When rod-shaped member 16 makes contact with the underside of a stationary belt 110 downward pressure is exerted by belt 110 on a central region of rod-shaped member 16 (FIG. 7) such that end 96 of rod-shaped member 16 bends slightly upward as shown. Because of the movement of rod-shaped member in direction 90 against belt 110, rod-shaped member 16 rotates in the direction of arrow 112.

Figure 6:
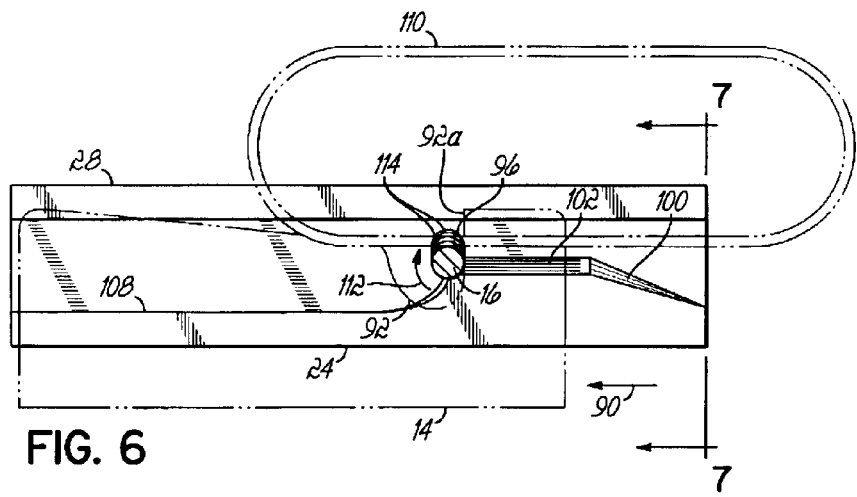
Figure 7:
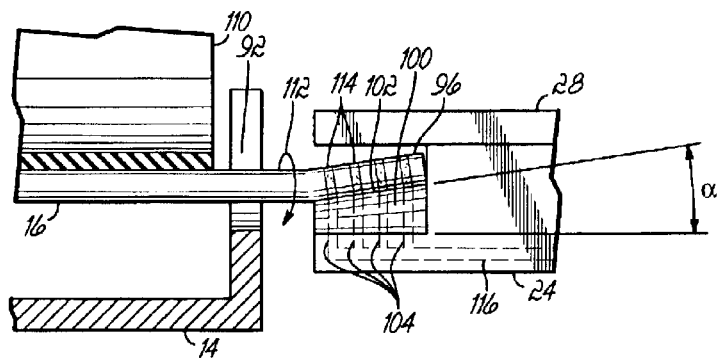
FIG. 7 is a cross sectional view taken along line 7—7 of FIG. 6.
Figure 8:
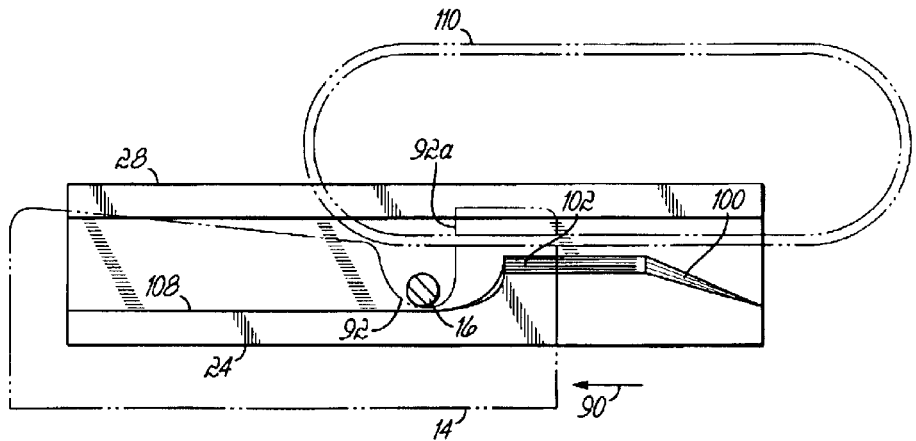
FIG. 8 is a schematic side cross sectional view similar to FIGS. 3–6, but illustrating the position of the cotton swab stick completely downstream of the adhesive application surface.

As shown in FIGS. 6 and 7, end 96 travels along and contacts adhesive application surface 102. When end 96 is positioned at the upstream end of surface 102, adhesive 114 is discharged through passages 104 by actuating valve 32 in response to a signal previously sent to a control (not shown) by sensor 80 (FIG. 1). This adhesive 114 makes contact with end 96 and is then spread preferably around the entire circumference of end 96 as it travels downstream on surface 102 to the position shown in FIGS. 6 and 7. Application surface 102 is preferably angled toward carrier 14 as shown in FIG. 7 to ensure full contact between end 96 and surface 102 along the entire length of end 96. This angle α is preferably about 4°–6°. Grooves 106 help ensure that bands of adhesive 14 are formed with uniform width and depth. Preferably, grooves 106 are 0.1 mm deep, 1 mm wide and about 15 mm long when manufacturing conventional cotton swabs with conventional cold glue used for that purpose. Approximately 0.65 mg of adhesive is applied to end 96. This adhesive is supplied to respective discharge passages 104 from a supply passage 116 (FIG. 7) which communicates with valve 32. As shown in FIG. 8, when rod-shaped member 16 travels completely past application surface 102, it drops down to the bottom of slot 92 yet stays at a level above surface 108 so that adhesive bands 114 remain intact and undisturbed. Cotton fibers and/or other components may then be secured via adhesive bands 114 at a downstream station (not shown).

While the present invention has been illustrated by a description of various embodiments and while these embodiments have been described in considerable detail, it is not the intention of the applicants to restrict or in any way limit the scope of the appended claims to such detail. As one example, it will be appreciated that while the adhesive discharge passages are shown to be oriented upward, one or more discharge passages may be oriented in another direction, such as downward. Using a downward orientation can, for example, allow for easier clean-up and maintenance, and may provide additional mounting space in many applications. Additional advantages and modifications will readily appear to those skilled in the art. The invention in its broader aspects is therefore not limited to the specific details, representative apparatus and method, and illustrative example shown and described. According, departures may be made from such details without departing from the spirit or scope of applicants' general inventive concept.

Having described the invention, what is claimed is:

1. A system for applying adhesive to at least a first end of a rod shaped member having a longitudinal axis, comprising:
    a carrier configured to convey the rod shaped member in a machine direction while allowing rotation of the rod shaped member about the longitudinal axis thereof,
    a first adhesive applicator including a first adhesive application surface positioned to engage the first end of the rod shaped member, and at least a first adhesive discharge passage positioned to apply adhesive to the first end of the rod shaped member, said first adhesive application surface having at least a portion thereof substantially flat and extending in the machine direction downstream of said adhesive discharge passage to allow at least a substantially complete rotation of the first end thereon,
    a rotator device configured to rotate the rod shaped member about the longitudinal axis thereof as the rod shaped member is conveyed along said portion of said first adhesive application surface.

2. The system of claim 1, wherein said portion of said first adhesive application surface includes a plurality of grooves extending in the machine direction.

3. The system of claim 2, further comprising a plurality of adhesive discharge passages, each adhesive discharge passage being at least generally aligned with one of said grooves in the machine direction.

4. The system of claim 1, wherein said portion of said first adhesive application surface is angled toward said carrier.

5. The system of claim 1, wherein said carrier includes a slot configured to receive said rod shaped member and accommodate movement thereof between a first position used during conveying and a second position in which the first end is rotating on said portion of said first adhesive application surface.

6. The system of claim 1, further comprising an inclined surface positioned upstream of said portion of said first adhesive application surface, said inclined surface configured to move said rod shaped member into engagement with said rotator device as the rod shaped member is conveyed toward said portion of said first adhesive application surface by said carrier.

7. The system of claim 1, wherein said adhesive discharge passage extends through said first adhesive application surface.

8. The system of claim 1, wherein said rotator device is a stationary frictional element configured to be in engagement with an area of the rod shaped member other than the first end as the first end is being conveyed along said portion of said first adhesive application surface.

9. The system of claim 1, wherein said carrier is a link on a chain-like conveying structure.

10. The system of claim 1, further comprising:
    a second adhesive applicator positioned on a side of said carrier opposite to said first adhesive applicator and having a second adhesive application surface positioned to engage a second end of the rod shaped member, and at least a second adhesive discharge passage positioned to apply adhesive to the second end of the rod shaped member.

11. The system of claim 1, further comprising:
    a dispensing valve operatively coupled with said first adhesive applicator to selectively supply adhesive to said first adhesive discharge passage, and
    a sensor operative to detect the rod shaped member and operatively coupled to said valve such that said valve causes adhesive to be dispensed through said first discharge passage as a result of said sensor detecting the rod shaped member.

12. A system for applying adhesive to at least a first end of a rod shaped member having a longitudinal axis, comprising:
    a carrier configured to convey the rod shaped member in a machine direction while allowing rotation of the rod shaped member about the longitudinal axis thereof,
    a first adhesive applicator including a first adhesive application surface positioned to engage the first end of the rod-shaped member, and at least a first adhesive discharge passage positioned to apply adhesive to the first end of the rod shaped member being conveyed by said carrier, a rotator device configured to rotate the rod shaped member about the longitudinal axis thereof as the rod shaped member is conveyed by said carrier past said first adhesive applicator, and engagement structure at least partially on the carrier and configured to move the rod shaped member in a direction transverse to the machine direction.

13. The system of claim 12, wherein said engagement structure includes an inclined surface positioned upstream of said first adhesive application surface, said inclined surface configured to move said rod shaped member into engagement with said rotator device as the rod shaped member is conveyed toward said first adhesive applicator by said carrier.

14. The system of claim 13, wherein said engagement structure further includes a slot in said carrier which receives the rod shaped member, the rod shaped member moving within said slot as the rod shaped member moves up said inclined surface.

15. The system of claim 12, wherein said rotator device is a stationary frictional element configured to be in engagement with the rod shaped member as the rod shaped member is being conveyed past said first adhesive applicator.

16. The system of claim 12, wherein said carrier is a link on a chain-like conveying structure.

17. The system of claim 12, further comprising:
a second adhesive applicator positioned on a side of said carrier opposite to said first adhesive applicator and configured to apply adhesive to a second end of the rod shaped member.

18. The system of claim 12, further comprising:
a dispensing valve operatively coupled with said first applicator to selectively supply adhesive to said first adhesive discharge passage, and
a sensor operative to detect the rod shaped member and operatively coupled to said dispensing valve such that said valve causes adhesive to be dispensed through said first discharge passage as a result of said sensor detecting the rod shaped member.

19. A system for applying adhesive to at least a first end of a rod shaped member having a longitudinal axis, comprising:
a carrier configured to convey the rod shaped member in a machine direction while allowing rotation of the rod shaped member about the longitudinal axis thereof,
a first adhesive applicator including a first adhesive application surface angled toward said carrier for engagement with the first end of the rod shaped member, and at least a first adhesive discharge passage communicating with said first adhesive application surface to apply adhesive to the first end of the rod shaped member, and
a rotator device configured to rotate the rod shaped member about the longitudinal axis thereof as the rod shaped member is conveyed along said first adhesive application surface.

20. The system of claim 19, wherein said first adhesive application surface includes grooves extending in the machine direction.

21. The system of claim 19, wherein said carrier includes a slot configured to receive said rod shaped member and accommodate movement thereof between a conveying position and an adhesive application position.

22. The system of claim 19, further comprising an inclined surface positioned upstream of said first adhesive application surface, said inclined surface configured to move the rod shaped member into engagement with said rotator device as the rod shaped member is conveyed toward said first adhesive application surface by said carrier.

23. The system of claim 19, further comprising a plurality of adhesive discharge passages spaced transversely on said first adhesive application surface relative to the machine direction.

24. The system of claim 19, wherein said rotator device is a stationary frictional element configured to be in engagement with an area of the rod shaped member other than the first end as the first end is being conveyed along said first adhesive application surface.

25. The system of claim 19, wherein said carrier is a link on a chain-like conveying structure.

26. The system of claim 19, further comprising:
a second adhesive applicator positioned on a side of said carrier opposite to said first adhesive applicator and having a second adhesive application surface positioned to engage a second end of the rod shaped member, and at least a second adhesive discharge passage communicating with said second adhesive application surface to apply adhesive to the second end of the rod shaped member.

27. The system of claim 19, further comprising:
a dispensing valve operatively coupled with said first adhesive applicator to selectively supply adhesive to said first adhesive discharge passage, and
a sensor operative to detect the rod shaped member and operatively coupled to said valve such that said valve causes adhesive to be dispensed through said first discharge passage as a result of said sensor detecting the rod shaped member.

28. A system for applying adhesive to at least a first end of a rod shaped member having a longitudinal axis, comprising:
a carrier configured to convey the rod shaped member in a machine direction while allowing rotation of the rod shaped member about the longitudinal axis thereof,
a first adhesive applicator including a first adhesive application surface positioned to engage the first end of the rod shaped member, and at least a first adhesive discharge passage communicating with said first adhesive application surface to apply adhesive to the first end of the rod shaped member, and
a rotator device positioned on a generally opposite side of the rod shaped member relative to said first adhesive application surface, said rotator device configured to rotate the rod shaped member about the longitudinal axis thereof as the rod shaped member is conveyed along said first adhesive application surface.

* * * * *